US00PP21775P2

(12) United States Plant Patent
Pronk et al.

(10) Patent No.: US PP21,775 P2
(45) Date of Patent: Mar. 8, 2011

(54) ***HEUCHERA* PLANT NAMED 'BIG TOP GOLD'**

(50) Latin Name: *Heuchera villosa*
Varietal Denomination: Big Top Gold

(75) Inventors: Teunis Johannes Pronk, MJ Hoofddorp (NL); Janmark Van Duijn, JE Noordwijk (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/592,138

(22) Filed: Nov. 19, 2009

(51) Int. Cl.
*A01H 5/00* (2006.01)

(52) U.S. Cl. ..... Plt./440

(58) Field of Classification Search ..... Plt./440
See application file for complete search history.

*Primary Examiner*—June Hwu
(74) *Attorney, Agent, or Firm*—Audrey Charles

(57) ABSTRACT

A new and distinct cultivar of *Heuchera* plant named 'Big Top Gold', characterized by its large orbicular-shaped leaves that emerge a dark browned yellow-green and mature with increased dark yellow-green coloration, large inflorescences; and vigorous, mounded growth habit, is disclosed.

1 Drawing Sheet

Latin name of genus and species of plant claimed: *Heuchera villosa.*

Variety denomination: 'Big Top Gold'.

BACKGROUND OF THE INVENTION

The present invention relates to a new and distinct cultivar of *Heuchera* plant botanically known as *Heuchera villosa* and hereinafter referred to by the cultivar name 'Big Top Gold'.

The new *Heuchera* cultivar is a polyploid of *Heuchera* 'Caramel', U.S. Plant Pat. No. 16,560. The polyploidy was induced under laboratory conditions using a colchicine treatment on in vitro plants. Plantlets from the treatment were trialed in a controlled environment at Hillegom, The Netherlands. *Heuchera* 'Big Top Gold' was discovered and selected as a single flowering plant from the population of treated plants during July 2007.

Asexual reproduction of the new cultivar by in vitro propagation since November 2007 at Hillegom, The Netherlands has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Big Top Gold' as a new and distinct cultivar of *Heuchera* plant:

1. Large orbicular-shaped leaves that emerge a greyed-orange and mature to a yellow-green coloration;
2. Large inflorescences; and
3. Moderately vigorous, mounded growth habit.

Of the many commercially available *Heuchera* cultivars, the most similar in comparison to the new cultivar is the parent cultivar 'Caramel', U.S. Plant Pat. No. 16,560. However, in side by side comparisons, plants of the new cultivar differ from plants of 'Caramel' in at least the following characteristics:

1. Plants of the new cultivar have larger leaves than plants of 'Caramel'; and

2. Plants of the new cultivar have larger inflorescences than plants of 'Caramel'.

While the leaf margins of both the parent and the new cultivar are crenate, it was unexpected to observe the plants of the new cultivar have leaf margins with a more undulating appearance those of the parent plant.

In addition, the new cultivar is similar in comparison to 'Big Top Burgundy' (U.S. patent application Ser. No. 12/592,147) and 'Big Top Bronze' (U.S. patent application Ser. No. 12/592,082), co-pending U.S. Plant Patent applications. However, in side by side comparisons, plants of the new cultivar differ from plants of 'Big Top Burgundy' and 'Big Top Bronze' primarily in foliage color.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Big Top Gold'. The plants were grown in 5 gallon containers for 2 years in a greenhouse located in Hillegom, The Netherlands.

DETAILED BOTANICAL DESCRIPTION

Figure 1:
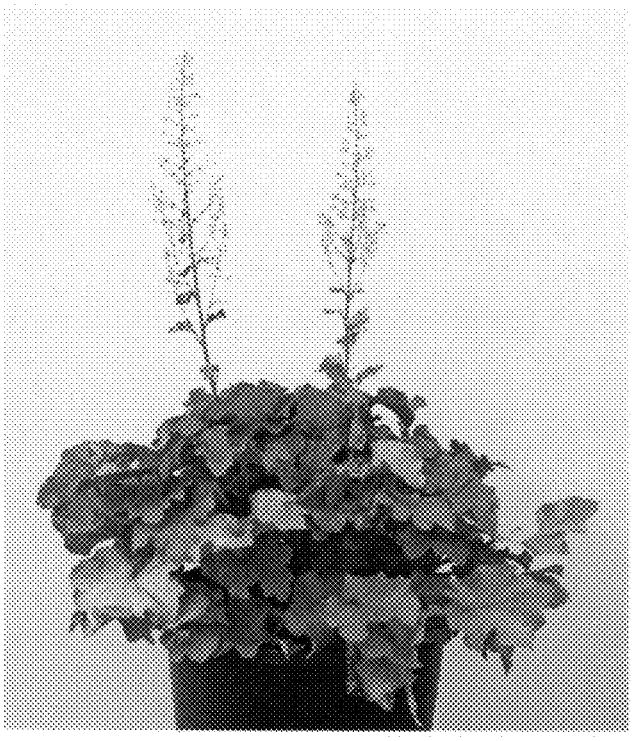
FIG. 1 illustrates a side view of the overall growth and flowering habit of 'Big Top Gold'.
Figure 2:
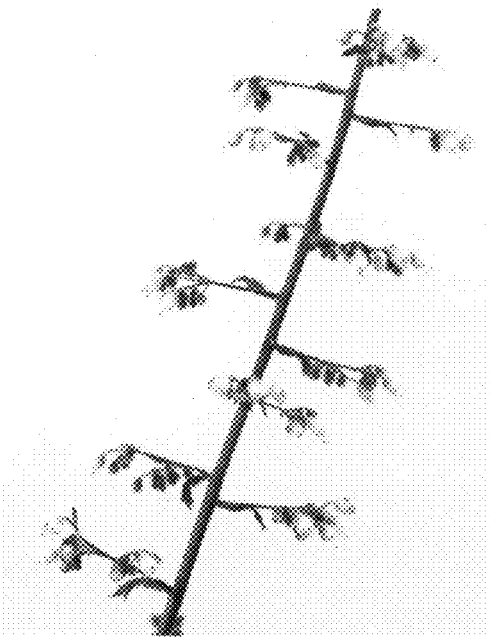
FIG. 2 illustrates a close-up view of an individual inflorescence of 'Big Top Gold'.
Figure 3:
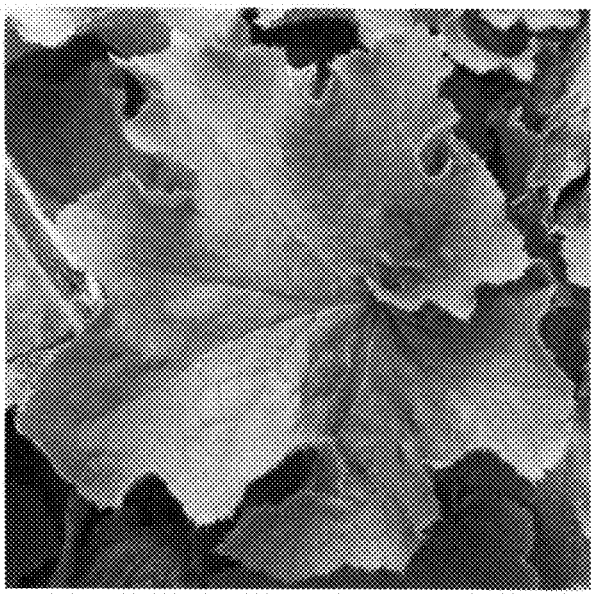
FIG. 3 illustrates a close-up view of the foliage of 'Big Top Gold'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in August 2009 under natural light conditions in Hillegom, The Netherlands.

The following descriptions and measurements describe plants produced from in vitro propagated plants and grown in 5 gallon containers for 2 years in a plastic-covered greenhouse located in Hillegom, The Netherlands. The plants were grown under conditions comparable to those used in commercial practice having average day temperatures of 18° C. to 25° C. and average night temperatures of 4° C. to 8° C. Measurements and numerical values represent averages of typical plants.

Botanical classification: *Heuchera villosa* cultivar 'Big Top Gold'.

Parentage:

*Parent.*—*Heuchera* 'Caramel', U.S. Plant Pat. No. 16,560.

Propagation:

*Type.*—In vitro propagation is preferred, divisions are possible.

*Time to initiate roots in vitro.*—Approximately 10 days at 20° C.

*Time to initiate roots in greenhouse.*—Approximately 20 days at 20° C.

*Time to produce a rooted plantlet in summer.*—Approximately 42 days.

*Root description.*—Fine, fibrous; white to ivory in color.

*Rooting habit.*—Freely branching.

Plant description:

*Commercial crop time.*—Approximately 20 weeks from a rooted tissue culture plantlet to finish in a 1 gallon container.

*Growth habit and general appearance.*—Clump-forming herbaceous perennial, mounded foliage.

*Growth rate.*—Moderately vigorous, approximately 10 cm per month in spring.

*Outdoor plant performance.*—Use as bedding plants or in mixed-container plantings; at least tolerant to temperatures up to 35° C. and hardy to USDA zone 3.

*Size.*—Height from soil level to top of plant plane: Approximately 71.9 cm. Height from soil level to top of foliage: Approximately 31.9 cm. Width: Approximately 65.7 cm.

*Branching habit.*—No branching, basal rosettes of leaves on petioles form a short stem-like structure. Number of rosettes per plant: Approximately 2.

*Stems.*—Strength: Strong. Shape: Rounded. Length: Approximately 6.6 cm. Diameter: Approximately 1.6 cm. Length of central internode: Approximately 3.0 mm. Texture: Smooth, slightly glossy. Color of young and mature stem: 150C.

Foliage description:

*General description.*—Moderately durable to environmental stresses. Quantity of leaves per rosette: Approximately 17. Fragrance: None. Form: Simple. Arrangement: Alternate.

*Leaves.*—Aspect: Blade is nearly perpendicular to petiole. Shape: Orbicular. Margin: Crenate, lobed with an average of 7 lobes per leaf. Apex: Abruptly acute. Base: Hastate, moderately overlapping. Venation pattern: Laciniate. Length of mature leaf: Approximately 13.2 cm. Width of mature leaf: Approximately 13.3 cm. Texture of upper surface: Dull, slightly rough. Sparsely pubescent with short hairs. Texture of lower surface: Dull, slightly rough. Densely pubescent with short hairs on venation. Length of pubescence: Approximately 1.75 mm. Color of pubescence: 156D and lighter. Color of upper surface of young foliage: N167A with 164A to 164B. Color of lower surface of young foliage: 182A. Color of upper surface of mature foliage: 152D with 153A to 153B with venation of 145D. Color of lower surface of mature foliage: 181C to 181D with venation of 181C to 181D.

*Stipules.*—Two leafy stipules located at the base of each leaf. Apex: Narrow acute. Length: Approximately 1.9 cm. Width: Approximately 3.0 mm. Color: 187B to 187C.

*Petiole.*—Length: Approximately 23.3 cm. Diameter: Approximately 4.0 mm. Texture: Densely pubescent. Length of pubescence: Approximately 3 mm. Color of pubescence: 156D and lighter. Color of petiole: 183D.

Flowering description:

*Flowering habit.*—'Big Top Gold' flowers once a year during late spring to midsummer under outdoor conditions.

*Lastingness of individual flower on the plant.*—Approximately 7 days.

Inflorescence description:

*General description.*—Type: Compound spike emerging from the base of the rosette. Fragrance: Faint, sweet. Length or height including the peduncle: Approximately 71.4 cm. Width: Approximately 10.8 cm. Quantity of flowers per inflorescence: Approximately 275. Quantity of fully open flowers per rosette: Approximately 200. Quantity of flower buds per rosette: Approximately 75.

*Peduncle and rachis.*—Strength: Moderate. Aspect: Approximately 20° angle from vertical. Length: Approximately 69.8 cm. Diameter at midpoint: Approximately 3.0 mm. Texture: Glabrous. Color: 152A to 152B.

Flower description:

*General description.*—Type: Single, campanulate, self-cleaning. Aspect: Drooping to slightly outward.

*Bud.*—Rate of opening: Generally takes 3 days for bud to progress from first color to fully open flower.

*Bud just before opening.*—Shape: Broadly obovate. Length: Approximately 4.0 mm. Diameter: Approximately 3.0 mm. Color: 155A with base of 174C to 174D.

*Corolla.*—Shape: Campanulate. Diameter: Approximately 5.0 mm Depth: Approximately 6.0 mm.

*Petals.*—Quantity: 5. Arrangement: Rotate. Shape: Narrowly obovate. Appearance: Dull. Margin: Entire. Apex: Acute. Base: Lower half fused into hypanthium. Length: Approximately 3.5 mm. Width: Approximately 0.75 mm. Texture of upper and lower surfaces: Glabrous. Color of upper and lower surface when first open: NN155C. Color of upper and lower surfaces when fully open: NN155C.

*Calyx.*—Shape: Cup. Length: Approximately 4.0 mm. Diameter: Approximately 4.0 mm.

*Sepals.*—Quantity per flower: 5. Shape: Obovate. Appearance: Dull. Margin of free portion: Entire. Apex: Broadly acute. Base: Lower half fused into hypanthium. Length: Approximately 4.0 mm. Width at rim of hypanthium: Approximately 1.5 mm. Texture: Densely pubescent with short glandular hairs.

Length of pubescence: Approximately 0.3 mm. Color of pubescence: Closest to 60B to 60C. Color of upper surface of immature sepals: 145D and tips of 144C with 145B to 145C. Color of lower surface of immature sepals: 174C. Color of upper surface of mature sepals: 155D and tips of 144C to 144D. Color of lower mature surface of sepals: 150D with lower half strongly tinged with 152D and tips of 146C to 146D.

*Pedicel.*—Strength: Moderate. Aspect: The pedicel of the central flower of each spikelet is directly on top of the secondary pedicel, pedicels of secondary and tertiary flowers of each spikelet have an average 40° angle from vertical. Length: Approximately 4.0 mm Diameter: Approximately 0.5 mm. Texture: Glabrous. Color: 151C to 151D.

*Reproductive organs.*—Androecium: Quantity: 5 per flower. Anther shape: Ovate. Anther length: Approximately 1.2 mm. Anther color: 22B. Filament length: Approximately 3.0 mm. Filament color: N155B to N155C. Pollen amount: Sparse. Pollen color: 22A to 22B. Gynoecium: Pistil quantity: 2 per flower. Pistil length: Approximately 5.0 mm. Stigma shape: Pointed. Stigma color: 157D. Style length: Approximately 4.5 mm. Style color: N155B to N155C. Ovary color: 144C.

Seed and fruit production: Neither seed nor fruit production has been observed.

Disease and pest resistance: Resistance to pathogens and pests common to *Heuchera* has not been observed.

What is claimed is:

1. A new and distinct cultivar of *Heuchera* plant named 'Big Top Gold', substantially as herein shown and described.

* * * * *